US009962068B2

United States Patent
Takahashi (10) Patent No.: US 9,962,068 B2
(45) Date of Patent: May 8, 2018

(54) IMAGE PICKUP SYSTEM AND CONTROL METHOD OF IMAGE PICKUP SYSTEM (71) Applicant: OLYMPUS CORPORATION, Tokyo (JP)

(72) Inventor: Hidetsugu Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 157 days.

(21) Appl. No.: 14/948,793

(22) Filed: Nov. 23, 2015

(65) Prior Publication Data

US 2016/0073865 A1   Mar. 17, 2016

Related U.S. Application Data (63) Continuation of application No. PCT/JP2014/061944, filed on Apr. 30, 2014.

(30) Foreign Application Priority Data

Jul. 9, 2013 (JP) .................... 2013-143801

(51) Int. Cl.
  *H04N 5/222*   (2006.01)
  *A61B 1/045*   (2006.01)
  (Continued)

(52) U.S. Cl.
  CPC .......... *A61B 1/045* (2013.01); *A61B 1/00006* (2013.01); *A61B 1/06* (2013.01);
  (Continued)

(58) Field of Classification Search
  None
  See application file for complete search history.

(56) References Cited

U.S. PATENT DOCUMENTS

2008/0232130 A1* 9/2008 Suda .................. A61B 1/045
                                                      362/574
2009/0147077 A1* 6/2009 Tani .................. A61B 1/042
                                                       348/68
(Continued)

FOREIGN PATENT DOCUMENTS

EP    2407087 A2    1/2012
EP    2407088 A2    1/2012
(Continued)

OTHER PUBLICATIONS

Author: Matsushita, Minoru Title: Translation of JP2002172088 Date: Jun. 2002.*

(Continued)

*Primary Examiner* — Twyler Haskins
*Assistant Examiner* — Wesley Chiu
(74) *Attorney, Agent, or Firm* — Scully, Scott, Murphy & Presser, P.C.

(57) ABSTRACT

An image pickup system includes a light emitting section that emits light for illuminating an object which operates periodically, an image pickup section including an image pickup device that performs an image pickup operation by a rolling shutter system, a period detection section that detects a period of motion of the object, a light emission signal generating section that outputs a stroboscopic light emission signal for causing the light emitting section to perform a stroboscopic light emission in synchronism with the period of the motion, a light emission period control section that sets as a light emission permission period, and a light emission non-permission period, and a light emission control section that performs control for causing the light emitting section to perform a light emission in the light emission permission period, and performs control for inhib-
(Continued)

iting a light emission of the light emitting section in the light emission non-permission period.

6 Claims, 7 Drawing Sheets

(51) Int. Cl.
| | | |
|---|---|---|
| A61B 1/06 | (2006.01) | |
| G03B 7/091 | (2006.01) | |
| G03B 15/05 | (2006.01) | |
| G02B 23/24 | (2006.01) | |
| H04N 5/225 | (2006.01) | |
| H04N 5/235 | (2006.01) | |
| H04N 5/353 | (2011.01) | |
| A61B 1/00 | (2006.01) | |
| A61B 1/267 | (2006.01) | |
| A61B 5/00 | (2006.01) | |
| A61B 7/00 | (2006.01) | |

(52) U.S. Cl.
CPC .......... *A61B 1/0684* (2013.01); *A61B 1/2673* (2013.01); *A61B 5/4803* (2013.01); *G02B 23/2461* (2013.01); *G03B 7/091* (2013.01); *G03B 15/05* (2013.01); *H04N 5/2256* (2013.01); *H04N 5/2354* (2013.01); *H04N 5/3532* (2013.01); *A61B 7/003* (2013.01)

(56) References Cited

U.S. PATENT DOCUMENTS

| | | | |
|---|---|---|---|
| 2010/0091177 | A1 | 4/2010 | Yonemitsu |
| 2011/0157416 | A1* | 6/2011 | Chen ................ H04N 5/235 348/227.1 |
| 2012/0016200 | A1 | 1/2012 | Seto et al. |
| 2012/0016201 | A1* | 1/2012 | Seto ................ A61B 1/045 600/180 |
| 2012/0057046 | A1* | 3/2012 | Tanaka ............. H04N 5/23212 348/229.1 |
| 2012/0071718 | A1* | 3/2012 | On .................. A61B 1/045 600/109 |
| 2012/0154629 | A1* | 6/2012 | Horiuchi ........... H04N 7/0127 348/226.1 |
| 2013/0201315 | A1* | 8/2013 | Takei ................ A61B 1/043 348/77 |

FOREIGN PATENT DOCUMENTS

| | | | |
|---|---|---|---|
| JP | 2002-172088 | A | 6/2002 |
| JP | 2002172088 | A * | 6/2002 |
| JP | 2008-229222 | A | 10/2008 |
| JP | 2009-136447 | A | 6/2009 |
| JP | 2010-093729 | A | 4/2010 |
| JP | 2012-019982 | A | 2/2012 |
| JP | 2012-019983 | A | 2/2012 |

OTHER PUBLICATIONS

International Search Report dated May 27, 2014 issued in PCT/JP2014/061944.

* cited by examiner

IMAGE PICKUP SYSTEM AND CONTROL METHOD OF IMAGE PICKUP SYSTEM

CROSS REFERENCE TO RELATED APPLICATION

This application is a continuation application of PCT/JP2014/061944 filed on Apr. 30, 2014 and claims benefit of Japanese Application No. 2013-143801 filed in Japan on Jul. 9, 2013, the entire contents of which are incorporated herein by this reference.

BACKGROUND OF THE INVENTION

1. Field of the Invention

The present invention relates to an image pickup system and a control method of the image pickup system, and in particular to an image pickup system and a control method of the image pickup system capable of performing stroboscopic photographing.

2. Description of the Related Art

There is conventionally known a technique for acquiring an image capable of visually recognizing a state of an object, which operates periodically (or vibrates periodically) such as vocal cords, in detail by performing stroboscopic photographing of the object.

Specifically, for example, in Japanese Patent Laid-Open Publication No. 2008-229222, there is disclosed a configuration for acquiring an image capable of observing an object which vibrates in a period shorter than an image pickup period of an image pickup unit in a substantially stationary state by controlling timing of performing stroboscopic light emissions by an LED and timing of image pickup by the image pickup unit.

SUMMARY OF THE INVENTION

An image pickup system according to an aspect of the present invention includes: a light emitting section configured to emit light for illuminating an object which operates periodically; an image pickup section configured to include an image pickup device that performs an image pickup operation by a rolling shutter system; a period detection section configured to detect a period of motion of the object; a light emission signal generating section configured to generate a stroboscopic light emission signal for causing the light emitting section to perform a stroboscopic light emission in synchronism with the period of the motion detected by the period detection section, and to output the stroboscopic light emission signal; a light emission period control section configured to set a first period in which exposure for obtaining an image of the same frame is performed on respective lines of the image pickup device, as a light emission permission period, and to set a second period in which exposure for obtaining images of different frames is performed on the respective lines of the image pickup device, as a light emission non-permission period; and a light emission control section configured to perform control for causing the light emitting section to perform a light emission when the stroboscopic light emission signal is inputted in the light emission permission period, and to perform control for inhibiting a light emission of the light emitting section when the stroboscopic light emission signal is inputted in the light emission non-permission period.

An image pickup method according to another aspect of the present invention includes: picking up an image of an object by an image pickup operation by a rolling shutter system; detecting a period of motion of the object; detecting a first period in which exposure for obtaining an image of the same frame is performed on respective lines of an image pickup device that performs the image pickup operation by the rolling shutter system, and a second period in which exposure for obtaining images of different frames is performed on the respective lines of the image pickup device; setting the first period as a light emission permission period in which a light emission by a light source that illuminates the object is permitted, and sets the second period as a light emission non-permission period in which a light emission by the light source is not permitted; and controlling the light source to emit illumination light only in the light emission permission period in synchronism with the motion.

DETAILED DESCRIPTION OF THE PREFERRED EMBODIMENTS

Hereinafter, embodiments of the present invention will be described referring to the drawings.

(First Embodiment)

Figure 1:
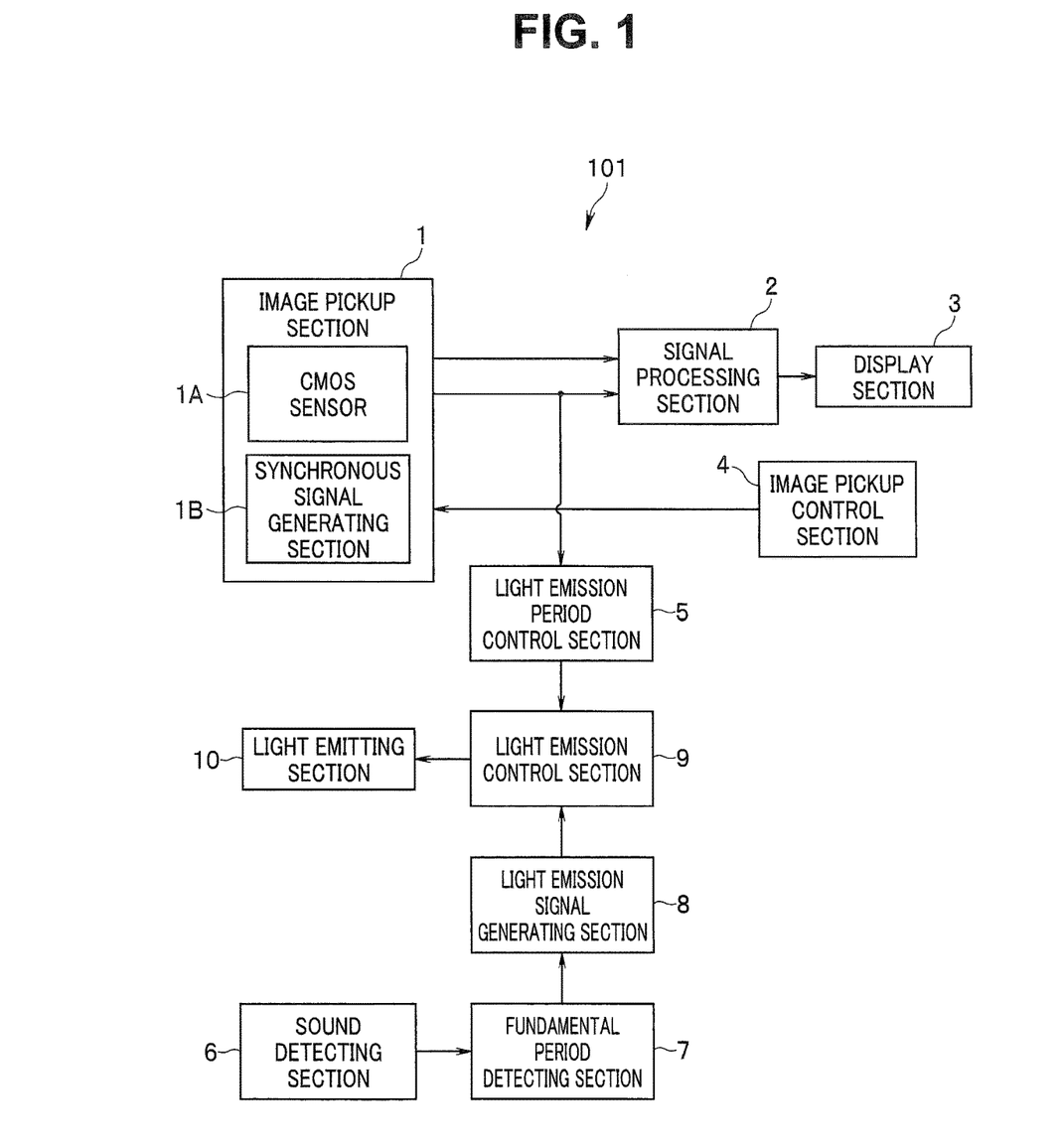
FIG. 1 is a diagram showing a configuration of a principal part of an image pickup system according to a first embodiment.
Figure 2:
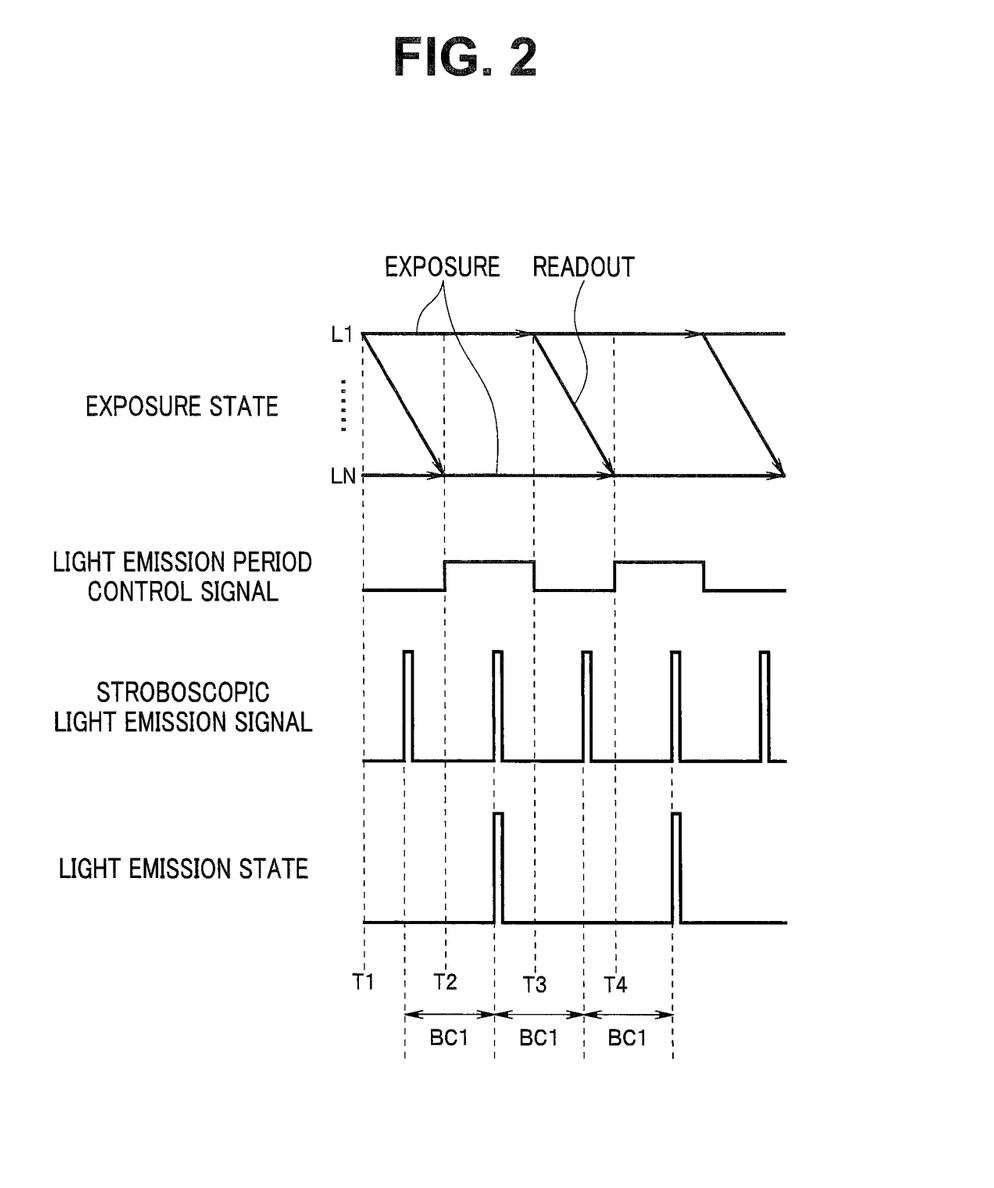
FIG. 2 is a diagram for explaining an example of an operation performed in the image pickup system according to the first embodiment.

FIG. 1 and FIG. 2 relate to a first embodiment of the present invention. FIG. 1 is a diagram showing a configuration of a principal part of an image pickup system according to the first embodiment.

An image pickup system 101, as shown in FIG. 1, is provided in an image pickup apparatus of an endoscope or the like, and includes an image pickup section 1 configured to pick up an image of an object and acquire the image, a signal processing section 2 configured to generate a video signal based on the image, and a display section 3 configured to display the image or the like in accordance with the image signal.

The image pickup section 1 is configured to include a CMOS image sensor (hereinafter abbreviated as "CMOS sensor") 1A that performs an image pickup operation (exposure and readout) by a rolling shutter system based on an image pickup control signal outputted from an image pickup control section 4 (as described later), acquires an image according to the image pickup operation, and outputs the image to the signal processing section 2, and a synchronous signal generating section 1B that generates a synchronous signal in synchronism with timing concerning the image pickup operation of the CMOS sensor 1A, and outputs the signal to the signal processing section 2 and a light emission period control section 5.

Based on the image and the synchronous signal outputted from the image pickup section 1, the signal processing section 2 performs predetermined processing of the image to generate the video signal, and outputs the generated video signal to the display section 3 at timing in accordance with the synchronous signal.

On the other hand, the image pickup system 101 includes the image pickup control section 4, the light emission period control section 5, a sound detecting section 6, a fundamental period detecting section 7, a light emission signal generating section 8, a light emission control section 9, and a light emitting section 10.

The image pickup control section 4 generates an image pickup control signal for causing the CMOS sensor 1A to acquire an image at a predetermined frame rate FRA (e.g. FRA=60 fps) by controlling an operation speed concerning the image pickup operation of the CMOS sensor 1A, and outputs the signal to the image pickup section 1. Further, when causing the CMOS sensor 1A to acquire an image at the predetermined frame rate FRA, the image pickup control section 4 controls the operation speed concerning the image pickup operation (exposure and readout) of the CMOS sensor 1A such that one light emission permission period (described later) is equal to or longer than 0.5/FRA second. Specifically, the image pickup control section 4 controls the operation speed concerning the image pickup operation (exposure and readout) of the CMOS sensor 1A such that one light emission permission period (described later) is equal to or longer than $1/120$ second when causing the CMOS sensor 1A to acquire an image at 60 fps.

The light emission period control section 5 detects an exposure state of the CMOS sensor 1A based on the synchronous signal outputted from the image pickup section 1. Further, the light emission period control section 5 sets a period in which exposure for obtaining an image of the same frame is performed on respective lines of the CMOS sensor 1A as a period of permitting a light emission (hereinafter also referred to as "light emission permission period") of the light emitting section 10 based on a detection result of the exposure state of the CMOS sensor 1A. A period in which exposure for obtaining images of different frames is performed on the respective lines of the CMOS sensor 1A is set as a period of not permitting a light emission (hereinafter also referred to as "light emission non-permission period") of the light emitting section 10. Then, the light emission period control section 5 generates a light emission period control signal capable of discriminating the light emission permission period and the light emission non-permission period, and outputs the signal to the light emission control section 9.

The sound detecting section 6 is provided with a sound collecting device such as a mike or a bone conduction device, and detects a sound generated by an object which performs a periodic operation (periodically vibrates) such as vocal cords, generates a sound signal having a signal level in accordance with intensity of the detected sound, and outputs the sound signal.

The fundamental period detecting section 7 detects a fundamental period (and a fundamental frequency) in accordance with a fundamental wave of the sound signal outputted from the sound detecting section 6, generates a fundamental period signal capable of specifying the detected fundamental period, and outputs the fundamental period signal to the light emission signal generating section 8.

The light emission signal generating section 8 specifies the fundamental period of the sound signal outputted from the sound detecting section 6 based on the fundamental period signal outputted from the fundamental period detecting section 7. Then, the light emission signal generating section 8 generates a stroboscopic light emission signal for causing the light emitting section 10 to perform stroboscopic light emissions for predetermined light emission periods and by a predetermined light amount based on the fundamental period specified as mentioned above, and outputs the stroboscopic light emission signal to the light emission control section 9.

When the stroboscopic light emission signal is inputted to the light emission control section 9 from the light emission signal generating section 8 within the light emission permission period indicated by the light emission period control signal outputted from the light emission period control section 5, the light emission control section 9 performs control for causing the light emitting section 10 to perform the light emission in accordance with the stroboscopic light emission signal. Further, when the stroboscopic light emission signal is inputted from the light emission signal generating section 8 within the light emission non-permission period indicated by the light emission period control signal outputted from the light emission period control section 5, the light emission control section 9 performs control for causing the light emitting section 10 not to perform the light emission.

The light emitting section 10 is provided with a light source capable of performing a stroboscopic light emission, such as an LED, and is configured to emit light for illuminating the object according to control of the light emission control section 9.

Subsequently, an operation performed in the image pickup system 101 will be described with respect to a case of picking up an image of vocal cords as an object, as an example. FIG. 2 is a diagram for explaining an example of an operation that is performed in the image pickup system according to the first embodiment.

Besides, for the sake of simplification, the following description is made assuming that timing at which exposure of one line of the CMOS sensor 1A is completed, timing at which readout of electric charges accumulated in respective pixels that belong to the one line is performed, and timing at which exposure on the one line is restarted are approximately simultaneous. Further, the following description is made assuming that it is configured such that the CMOS sensor 1A is provided with N lines of lines L1-LN, and each of the lines L1-LN is provided with P pixels.

A user arranges the image pickup section 1 and the sound detecting section 6 in the vicinity of the vocal cords which are periodically operating (vibrating), and thereby causes the CMOS sensor 1A to pick up an image of the vocal cords and the sound detecting section 6 to detect a sound generated by the vocal cords.

On the other hand, the synchronous signal generating section 1B generates the synchronous signal synchronized with the timing concerning the image pickup operation of the CMOS sensor 1A, and outputs the signal to (the signal processing section 2 and) the light emission period control section 5. Further, the fundamental period detecting section 7 detects the fundamental period in accordance with the fundamental wave of the sound signal outputted from the sound detecting section 6, and generates the fundamental period signal in accordance with the detected fundamental period and outputs the fundamental period signal to the light emission signal generating section 8.

The light emission period control section 5 detects the exposure state of the CMOS sensor 1A based on the synchronous signal outputted from the synchronous signal generating section 1B of the image pickup section 1, and further generates the light emission period control signal based on the detected exposure state of the CMOS sensor 1A.

Incidentally, as schematically shown in FIG. 2, in the image pickup operation by the rolling shutter system, for example, a first pixel located at one end of a line L1 is exposed at timing of time T1, second to (P-1)th pixels which are located at intermediate positions of the line L1 are sequentially exposed in a period after the time T1, and a Pth pixel located at the other end of the line L1 is exposed to timing of time T3. Then, at timing of time T3, readout of electric charges accumulated in respective pixels that belong to the line L1 are performed, and exposure on line L1 is restarted (from the first pixel).

On the other hand, as schematically shown in FIG. 2, in the image pickup operation by the rolling shutter system, for example, a first pixel located at one end of a line LN is exposed at timing of time T2 which is later than the time T1 by a predetermined time period, a second pixel to (P-1)th pixel which are located at intermediate positions of the line LN are sequentially exposed in a period after the time T2, and a Pth pixel located at the other end of line LN is exposed to timing of time T4 which is later than the time T3 by the predetermined time period. Then, at the timing of time T4, readout of electric charges accumulated in respective pixels that belong to the line LN is performed, and exposure on line LN is restarted (from the first pixel).

That is, according to the image pickup operation by the rolling shutter system as described above, a period from the time T2 to the time T3 can be treated as a period in which exposure for obtaining an image of the same frame is performed on the lines L1-LN of the CMOS sensor 1A. On the other hand, according to the image pickup operation by the rolling shutter system as described above, a period after the time T1 and before the time T2 and a period after the time T3 and before the time T4 can be treated as a period in which exposure for obtaining images of different frames is performed on the lines L1-LN of the CMOS sensor 1A.

Therefore, the light emission period control section 5 detects exposure states of the respective lines L1-LN from the time T1 to the time T4 (as an exposure state of the CMOS sensor 1A) based on synchronous signals outputted from the synchronous signal generating section 1B with the image pickup of the vocal cords by the image pickup section 1. Further, the light emission period control section 5 sets the period from the time T2 to the time T3 as a light emission permission period, and sets the period after the time T1 and before the time T2 and the period after the time T3 and before the time T4 as light emission non-permission periods. Then, the light emission period control section 5 generates the light emission period control signal such that a signal level for the light emission permission period and a signal level for the light emission non-permission period are made different, as shown in FIG. 2 as an example, and outputs the signal to the light emission control section 9.

On the other hand, the light emission signal generating section 8 specifies a fundamental period BC1 of the sound signal outputted from the sound detecting section 6 based on the fundamental period signal outputted from the fundamental period detecting section 7. Then, the light emission signal generating section 8 generates a stroboscopic light emission signal for causing the light emitting section 10 to perform a stroboscopic light emission at each fundamental period BC1, as shown in FIG. 2 as an example, and output the signal to the light emission control section 9.

The light emission control section 9 causes the light emitting section 10 to perform a light emission in accordance with the stroboscopic light emission signal when the stroboscopic light emission signal is inputted from the light emission signal generating section 8 in the period from the time T2 to the time T3, which is the light emission permission period indicated by the light emission period control signal outputted from the light emission period control section 5. On the other hand, when the stroboscopic light emission signal is inputted from the light emission signal generating section 8 in the period after the time T1 and before the time T2 and the period after the time T3 before the time T4, which are the light emission non-permission periods indicated by the light emission period control signal outputted from the light emission period control section 5, the light emission control section 9 causes the light emitting section 10 not to perform a light emission by nulling (the input of) the stroboscopic light emission signal. Thus, with the above control performed in the light emission control section 9, the light emitting section 10 performs light emissions in a light emission state shown in FIG. 2 as an example.

As described above, according to the image pickup system 101 of the present embodiment, the control is performed to cause the light emitting section 10 to perform the stroboscopic light emission during the period in which the exposure for obtaining an image of the same frame is performed on the lines L1-LN of the CMOS sensor 1A, whereas the control is performed to cause the light emitting section 10 not to perform the stroboscopic light emission during the period in which exposure for obtaining images of different frames is performed on the lines L1-LN of the CMOS sensor 1A. Therefore, according to the image pickup system 101 of the present embodiment, for example, in a case of observing an object which operates periodically (vibrates periodically) such as vocal cords in a pseudo still state by performing stroboscopic photographing of the object, it is possible to cause the display section 3 to display an image in which unevenness of brightness within one frame is suppressed.

That is, according to the image pickup system 101 of the present embodiment, when performing stroboscopic photographing of an object which operates periodically, deterioration of image quality which is caused by the image pickup operation by the rolling shutter system can be suppressed.

(Second Embodiment)

Figure 3:
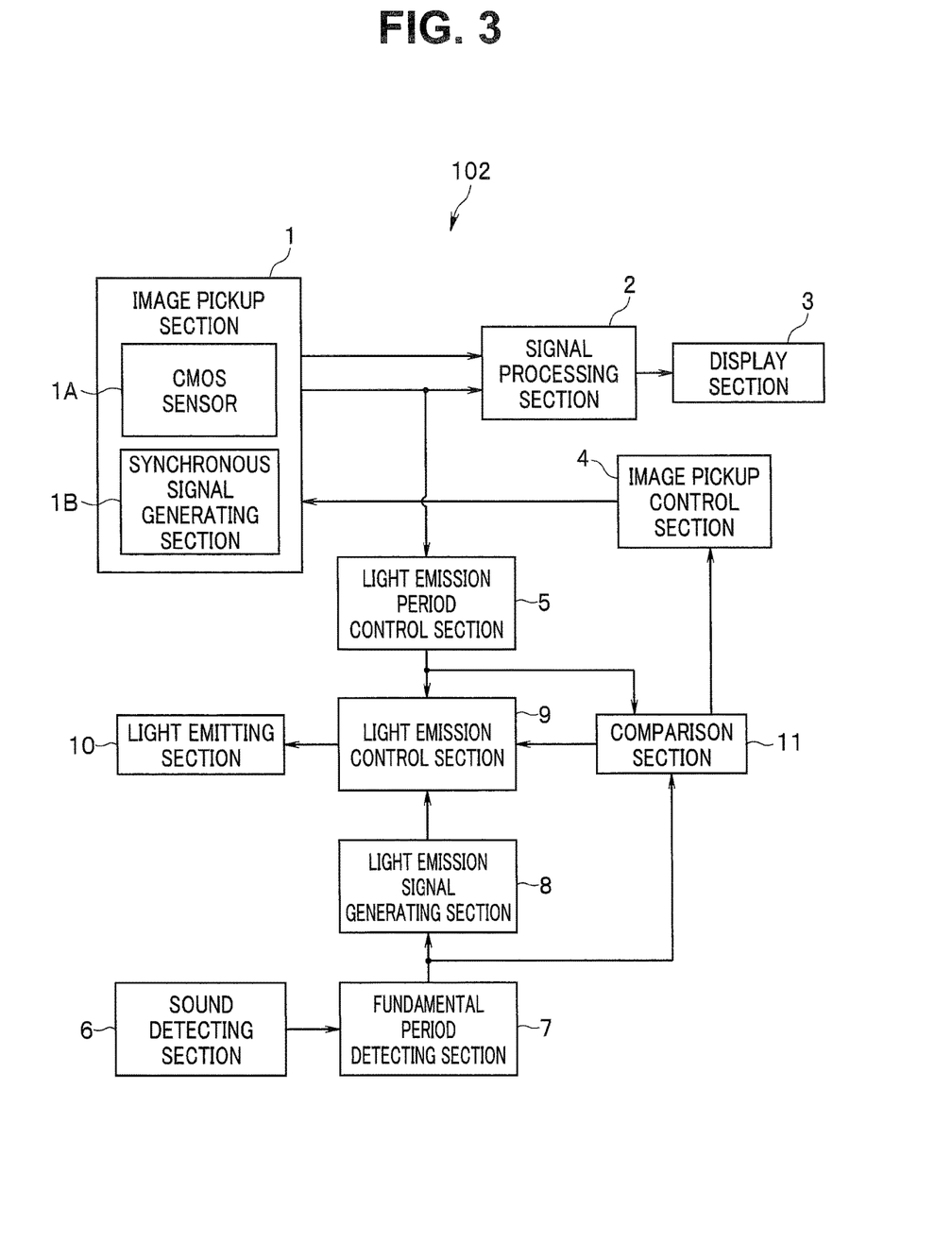
FIG. 3 is a diagram showing a configuration of a principal part of an image pickup system according to a second embodiment.
Figure 4:
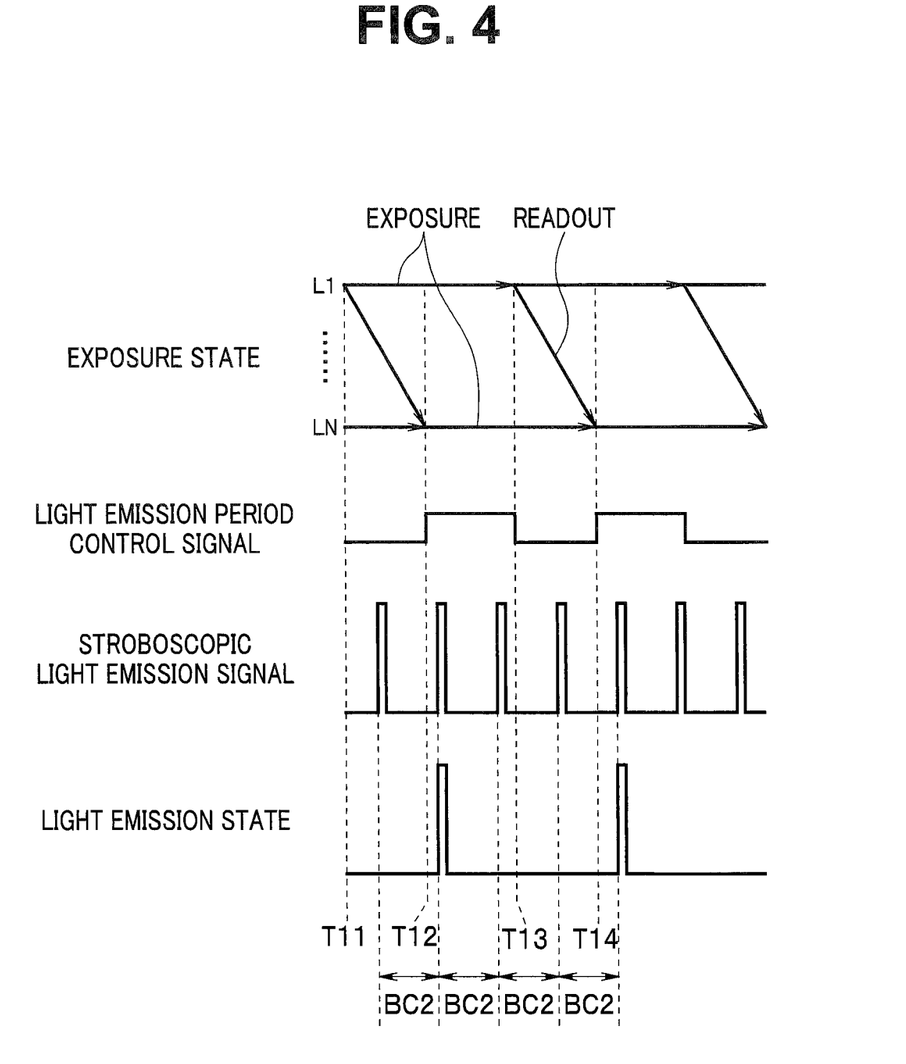
FIG. 4 is a diagram for explaining an example of an operation which is performed when a comparison result that a light emission permission period is longer than a fundamental period is obtained, in the image pickup system according to the second embodiment.
Figure 5:
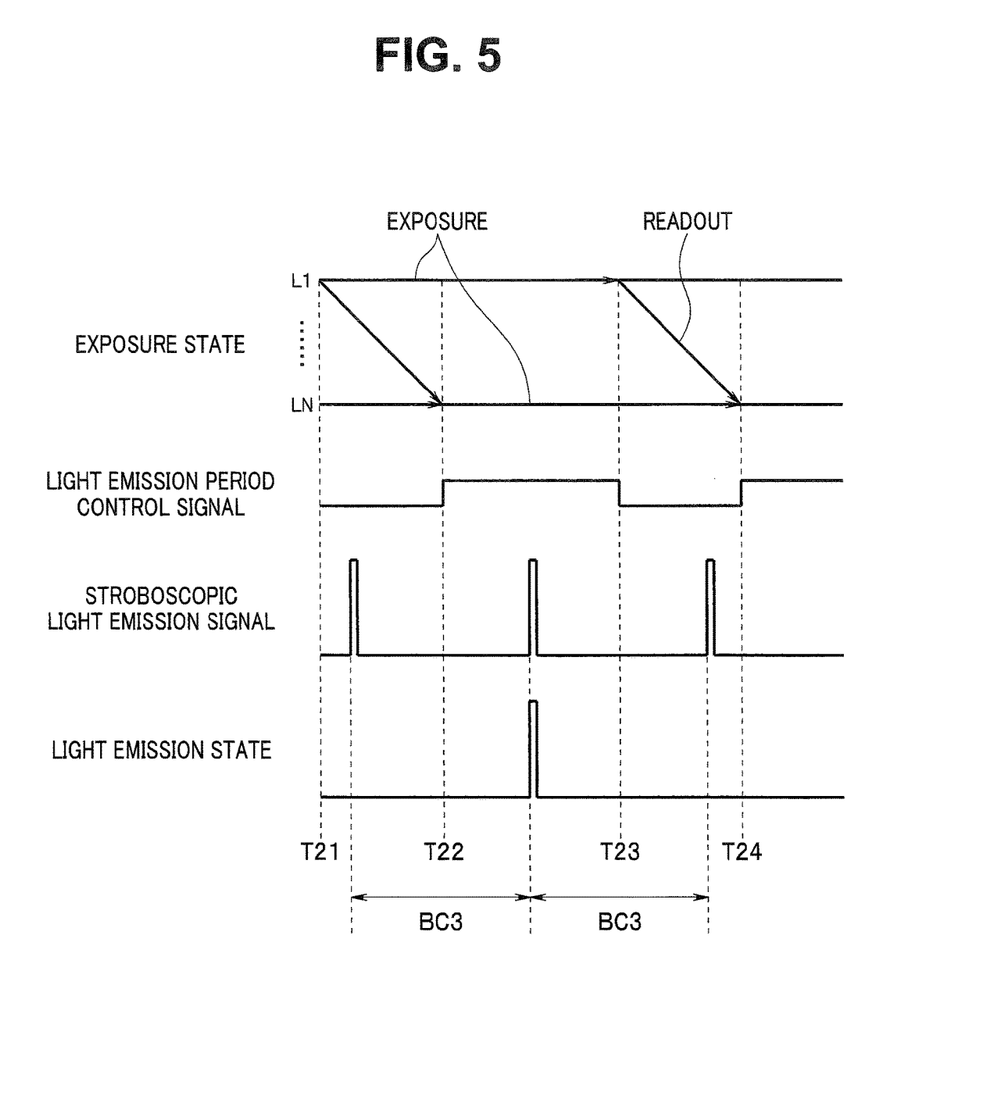
FIG. 5 is a diagram for explaining an example of an operation which is performed when a comparison result that the fundamental period is equal to or longer than the light emission permission period is obtained, in the image pickup system according to the second embodiment.

FIG. 3 to FIG. 5 relate to a second embodiment of the present invention. FIG. 3 is a diagram showing a configuration of a principal part of an image pickup system according to the second embodiment.

It is noted that in the present embodiment, a detailed description of a part having the same configuration as that in the first embodiment is omitted, and a part having configuration different from that of the first embodiment will be mainly described.

An image pickup system 102, as shown in FIG. 3, includes the image pickup section 1, the signal processing section 2, the display section 3, the image pickup control section 4, the light emission period control section 5, the sound detecting section 6, the fundamental period detecting section 7, the light emission signal generating section 8, the light emission control section 9, the light emitting section 10, and a comparison section 11.

The comparison section 11 specifies a light emission permission period based on the light emission period control signal outputted from the light emission period control section 5, and specifies the fundamental period of the sound signal outputted from the sound detecting section 6 based on the fundamental period signal outputted from the fundamental period detecting section 7.

Then, the comparison section 11 compares the light emission permission period and the fundamental period, and when a comparison result that the light emission permission period is longer than the fundamental period is obtained, the comparison section 11 generates a light emission limiting signal to limit the number of light emissions (the number of stroboscopic light emissions) of the light emitting section 10 in one light emission permission period to one, and outputs the light emission limiting signal to the light emission control section 9. Further, when the comparison section 11 compares the light emission permitting period and the fundamental period and a comparison result that the fundamental period is equal to or longer than the light emission permitting period is obtained, the comparison section 11 generates a frame rate limiting signal for reducing a frame rate concerning acquisition of an image by the CMOS sensor 1A to a half of the predetermined frame rate FRA, and outputs the frame rate limiting signal to the image pickup control section 4.

Next, an operation to be performed when the comparison result that the light emission permission period is longer than the fundamental period is obtained will be described referring to an example of a case of picking up an image of vocal cords as objects. FIG. 4 is a diagram for explaining an example of an operation that is performed when a comparison result that the light emission permission period is longer than the fundamental period is obtained, in the image pickup system according to the second embodiment.

A user arranges the image pickup section 1 and the sound detecting section 6 in the vicinity of the vocal cords which are periodically operating (vibrating), and thereby causes the CMOS sensor 1A to pick up an image of the vocal cords and the sound detecting section 6 to detect a sound generated by the vocal cords.

The synchronous signal generating section 1B generates the synchronous signal synchronized with timing concerning the image pickup operation of the CMOS sensor 1A, and outputs the signal to (the signal processing section 2 and) the light emission period control section 5. Further, the fundamental period detecting section 7 detects the fundamental period in accordance with the fundamental wave of the sound signal outputted from the sound detecting section 6, and generates the fundamental period signal in accordance with the detected fundamental period and outputs the fundamental period signal to the light emission signal generating section 8.

Incidentally, as schematically shown in FIG. 4, in the image pickup operation by the rolling shutter system, for example, the first pixel located at one end of the line L1 is exposed at timing of time T11, the second to (P-1)th pixels which are located at intermediate positions of the line L1 are sequentially exposed in a period after the time T11, and the Pth pixel located at the other end of the line L1 is exposed to timing of time T13. Then, at timing of the time T13, readout of electric charges accumulated in respective pixels that belong to the line L1 are performed, and exposure on the line L1 is restarted (from the first pixel).

Further, as schematically shown in FIG. 4, in the image pickup operation by the rolling shutter system, for example, the first pixel located at one end of the line LN is exposed at timing of time T12 which is later than the time T11 by a predetermined time period, the second to (P-1)th pixels which are located at intermediate positions of the line LN are sequentially exposed in a period after the time T12, and the Pth pixel located at the other end of the line LN is exposed to timing of time T14 which is later than the time T13 by the predetermined time period. Then, at timing of the time T14, readout of electric charges accumulated in respective pixels that belong to the line LN are performed, and exposure on the line LN is restarted (from the first pixel).

That is, according to the image pickup operation by the rolling shutter system as described above, a period from the time T12 to the time T13 can be treated as the period in which exposure for obtaining an image of the same frame is performed on the lines L1-LN of the CMOS sensor 1A. On the other hand, according to the image pickup operation by the rolling shutter system as described above, a period after the time T11 and before the time T12 and a period after the time T13 and before the time T14 can be treated as the period in which exposure for obtaining images of different frames is performed on the lines L1-LN of the CMOS sensor 1A.

The light emission period control section 5 detects exposure states of the respective lines L1-LN from the time T11 to the time T14 (as an exposure state of the CMOS sensor 1A) based on the synchronous signal outputted from the synchronous signal generating section 1B with the image pickup of the vocal cords by the image pickup section 1. Further, the light emission period control section 5 sets the period from the time T12 to the time T13 as the light emission permission period, and sets the period after the time T11 and before the time T12 and the period after the time T13 and before the time T14 as the light emission non-permission period. Then, the light emission period control section 5 generates the light emission period control signal such that the signal level for the light emission permission period and the signal level for the light emission non-permission period are made different, as shown in FIG. 4 as an example, and outputs the signal to the light emission control section 9.

The light emission signal generating section 8 specifies a fundamental period BC2 of a sound signal outputted from the sound detecting section 6 based on a fundamental period signal outputted from the fundamental period detecting section 7. Then, the light emission signal generating section 8 generates the stroboscopic light emission signal for causing the light emitting section 10 to perform the stroboscopic light emission at each fundamental period BC2, as shown in FIG. 4 as an example, and output the signal to the light emission control section 9.

In the period from the time T12 to the time T13, the light emission control section 9 causes the light emitting section 10 to perform a light emission in accordance with (an input of) a first stroboscopic light emission signal, whereas the light emission control section 9 nulls (input of) a second stroboscopic light emission signal and subsequent stroboscopic light emission signals to cause the light emitting section 10 not to perform a light emission. Further, when the stroboscopic light emission signal is inputted from the light emission signal generating section 8 in the period after the time T11 and before the time T12 and the period after the time T13 before the time T14, the light emission control section 9 causes the light emitting section 10 not to perform a light emission by nulling (the input of) the stroboscopic light emission signal. Thus, with the above control performed in the light emission control section 9, the light emitting section 10 performs light emissions in a light emission state, as shown in FIG. 4 as an example.

Besides, in the operation of the image pickup system 102 as described above, when a comparison result that the light emission permitting period is more than twice as long as the fundamental period, that is, when two or more stroboscopic light emission signals are always outputted within one light emission permission period from the light emission signal generating section 8, instead of performing the control for limiting the number of light emissions (the number of stroboscopic light emissions) by the light emission control section 9, it may be configured such that control for reducing a light emission amount (stroboscopic light emission amount) per one light emission in accordance with a length of the fundamental period is performed by the light emission control section 9. Specifically, for example, when a comparison result that the light emission permitting period is more than three times as long as the fundamental period, that is, when three stroboscopic light emission signals are outputted within one light emission permission period from the light emission signal generating section 8, it may be configured such that a light emission limiting signal for reducing the stroboscopic light emission amount per one light emission to one-third thereof is outputted from the comparison section 11 to the light emission control section 9.

Subsequently, an operation that is performed when the comparison result that the fundamental period is equal to or longer than the light emission permission period is obtained will be described referring to an example of a case of picking up an image of the vocal cords as objects. FIG. 5 is a diagram for explaining an example of an operation that is performed when the comparison result that the fundamental period is equal to or longer than the light emitting period is obtained, in the image pickup system 102.

A user arranges the image pickup section 1 and the sound detecting section 6 in the vicinity of the vocal cords which are periodically operating (vibrating), and thereby causes the CMOS sensor 1A to pick up an image of the vocal cords and the sound detecting section 6 to detect a sound generated by the vocal cords.

The image pickup control section 4 reduces an operation speed concerning the exposure and the readout of the CMOS sensor 1A based on the frame rate limiting signal, and thereby generates an image pickup control signal for acquiring an image at a half (e.g. 30 fps) of the predetermined frame rate FRA, and outputs the image pickup control signal to the image pickup section 1.

The synchronous signal generating section 1B generates the synchronous signal in synchronism with timing concerning the image pickup operation of the CMOS sensor 1A, and outputs the signal to (the signal processing section 2 and) the light emission period control section 5. Further, the fundamental period detecting section 7 detects the fundamental period in accordance with the fundamental wave of the sound signal outputted from the sound detecting section 6, and generates the fundamental period signal in accordance with the detected fundamental period and outputs the fundamental period signal to the light emission signal generating section 8.

Incidentally, as schematically shown in FIG. 5, in the image pickup operation by the rolling shutter system, the first pixel located at one end of the line L1 is exposed at timing of time T21, the second to (P-1)th pixels which are located at intermediate positions of the line L1 are sequentially exposed in a period after the time T21, and the Pth pixel located at the other end of the line L1 is exposed to timing of time T23. Then, at timing of the time T23, readout of electric charges accumulated in respective pixels that belong to the line L1 are performed, and exposure on the line L1 is restarted (from the first pixel).

Further, as schematically shown in FIG. 5, in the image pickup operation by the rolling shutter system, the first pixel located at one end of the line LN is exposed at timing of time T22 which is later than the time T21 by a predetermined time period, the second to (P-1)th pixels which are located at intermediate positions of the line LN are sequentially exposed in a period after the time T22, and the Pth pixel located at the other end of the line LN is exposed to timing of time T24 which is later than the time T23 by the predetermined time period. Then, at timing of the time T24, readout of electric charges accumulated in respective pixels that belong to the line LN are performed, and exposure on the line LN is restarted (from the first pixel).

That is, according to the image pickup operation in the rolling shutter method as described above, a period from the time T22 to the time T23 can be treated as a period in which exposure for obtaining an image of the same frame is performed on the lines L1-LN of the CMOS sensor 1A. On the other hand, according to the image pickup operation by the rolling shutter system as described above, a period after the time T21 and before the time T22 and a period after the time T23 and before the time T24 can be treated as a period in which exposure for obtaining images of different frames is performed on the lines L1-LN of the CMOS sensor 1A.

The light emission period control section 5 detects exposure states of the respective lines L1-LN from the time T21 to the time T24 (as an exposure state of the CMOS sensor 1A) based on the synchronous signal outputted from the synchronous signal generating section 1B with the image pickup of the vocal cords by the image pickup section 1. Further, the light emission period control section 5 sets the period from the time T22 to the time T23 as the light emission permission period, and sets the period after the time T21 and before the time T22 and the period after the time T23 and before the time T24 as the light emission non-permission period. Then, the light emission period control section 5 generates the light emission period control signal such that the signal level for the light emission permission period and the signal level for the light emission non-permission period are made different, as shown in FIG. 5 as an example, and outputs the signal to the light emission control section 9.

The light emission signal generating section 8 specifies a fundamental period BC3 of a sound signal outputted from the sound detecting section 6 based on a fundamental period signal outputted from the fundamental period detecting section 7. Then, the light emission signal generating section 8 generates a stroboscopic light emission signal for causing the light emitting section 10 to perform a stroboscopic light emission at each fundamental period BC3, as shown in FIG. 5 as an example, and output the signal to the light emission control section 9.

The light emission control section 9 causes the light emitting section 10 to perform a light emission in accordance with the stroboscopic light emission signal when the stroboscopic light emission signal is inputted in the period from the time T22 to the time T23. Further, the light emission control section 9 causes the light emitting section 10 not to perform a light emission by nulling (the input of) the stroboscopic light emission signal when the stroboscopic light emission signal is inputted in the period after the time T21 and before the time T22 and the period after the time T23 and before the time T24. Thus, with the above control performed in the light emission control section 9, the light emitting section 10 performs light emissions in a light emission state, as shown in FIG. 5 as an example.

As described above, according to the image pickup system 102 of the present embodiment, the control is performed to cause the light emitting section 10 to perform the stroboscopic light emission in the period in which the exposure for obtaining an image of the same frame is performed on the lines L1-LN of the CMOS sensor 1A, whereas the control is performed to cause the light emitting section 10 not to perform the stroboscopic light in the period in which the exposure for obtaining images of different frames is performed on the lines L1-LN of the CMOS sensor 1A. Therefore, according to the image pickup system 102 of the present embodiment, for example, in a case of observing an object which moves periodically (vibrates periodically) such as vocal cords in a pseudo still state by performing stroboscopic photographing of the object, it is possible to cause the display section 3 to display an image in which unevenness of brightness within one frame is suppressed.

On the other hand, according to the image pickup system 102 of the present embodiment, when the comparison result that the light emission permitting period is longer than the fundamental period is obtained by the comparison section 11, the number of stroboscopic light emissions or the stroboscopic light emission amount of the light emitting section 10 is limited, and thereby it is possible to prevent generation of an image in an overexposure state as much as possible. Further, according to the image pickup system 102 of the present embodiment, when the comparison result that the fundamental period is equal to or longer than the light emission permitting period is obtained by the comparison section 11, the frame rate concerning the acquisition of the image is reduced from the predetermined frame rate FRA, and thereby it is possible to prevent generation of an image in an underexposure state as much as possible. Therefore, according to the image pickup system 102 of the present embodiment, for example, in the case of observing the object which moves periodically (vibrates periodically) such as vocal cords in a pseudo still state by performing stroboscopic photographing of the object, it is possible to cause the display section 3 to display an image in which unevenness of brightness within one frame is suppressed.

That is, according to the image pickup system 102 of the present embodiment, when performing stroboscopic photographing of the object which operates periodically, deterioration of image quality which is caused by the image pickup operation by the rolling shutter system can be suppressed.

(Third Embodiment)

Figure 6:
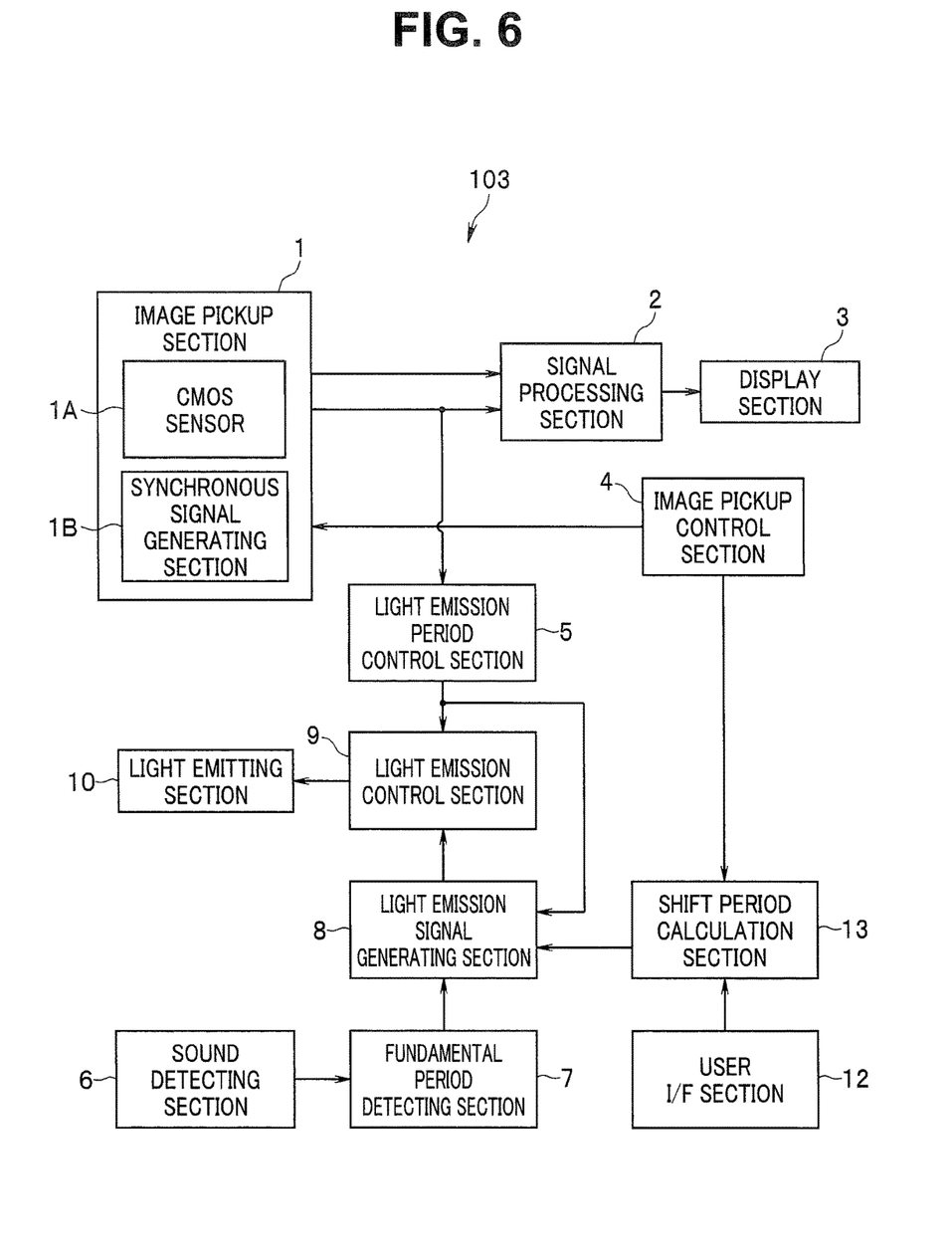
FIG. 6 is a diagram showing a configuration of a principal part of an image pickup system according to a third embodiment.
Figure 7:
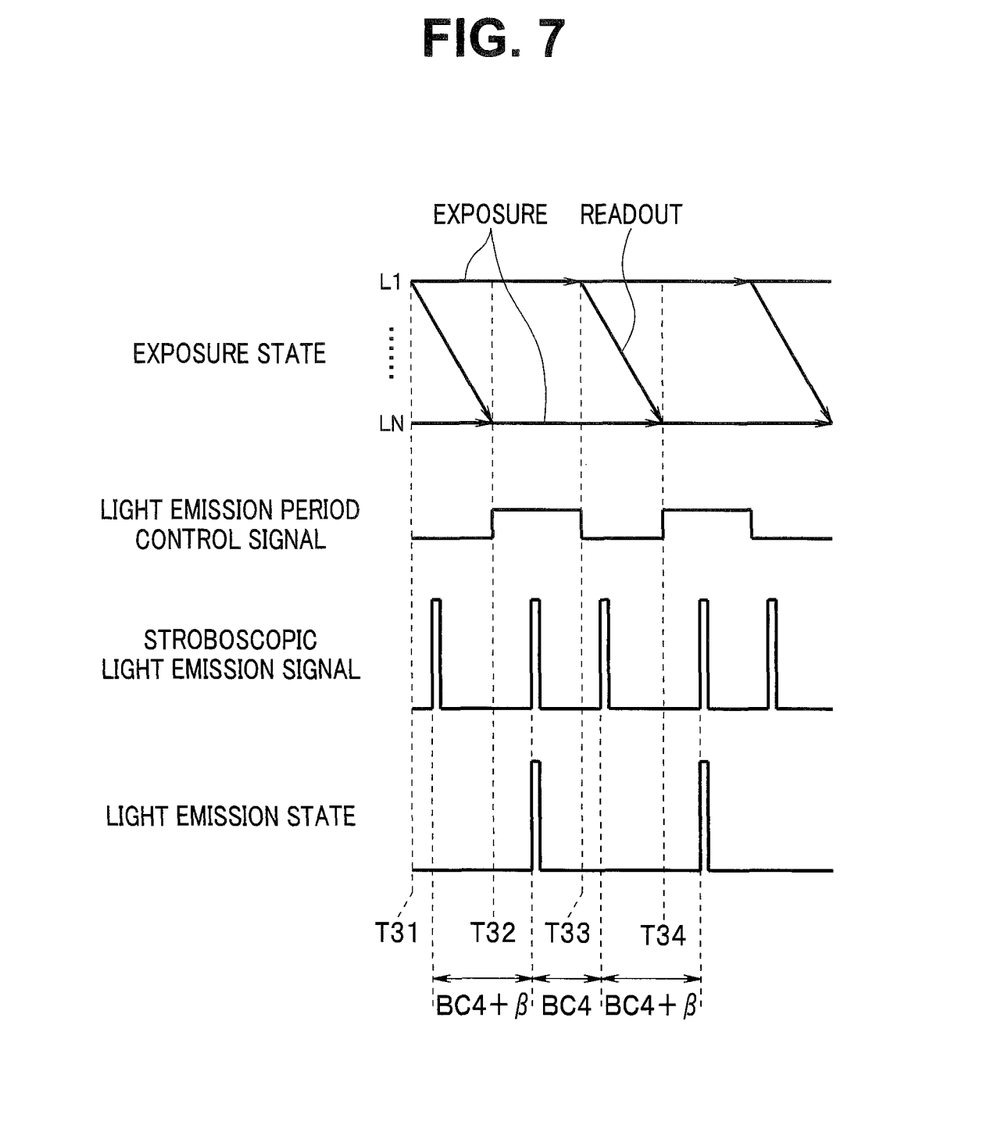
FIG. 7 is a diagram for explaining an example of an operation performed in the image pickup system according to the third embodiment.

FIG. 6 and FIG. 7 relates to a third embodiment of the present invention. FIG. 6 is a diagram showing a configuration of a principal part of an image pickup system according to the third embodiment.

It is noted that in the present embodiment, a detailed description of a part having the same configuration as that in at least one of the first and second embodiments is omitted, and a part having configuration different from that of the first and second embodiments will be mainly described.

An image pickup system 103, as shown in FIG. 6, includes the image pickup section 1, the signal processing section 2, the display section 3, the image pickup control section 4, the light emission period control section 5, the sound detecting section 6, the fundamental period detecting section 7, the light emission signal generating section 8, the light emission control section 9, the light emitting section 10, a user interface section (hereinafter abbreviated as "user I/F section") 12, and a shift period calculation section 13.

The user I/F section 12 is provided with an input device such as a touch panel or a keyboard, and it is configured that the user I/F section 12 is capable of setting, when observing an object which operates periodically (vibrates periodically) such as vocal cords, a slow-motion display rate SDR which is a value indicating the number of frames per second at which motion of the object displayed on the display section 3 is caused to shift. Specifically, for example, when causing the motion of the object displayed on the display section 3 to shift by two frames per second, a value of the slow-motion display rate SDR is set as "2". On the other hand, the user I/F section 12 outputs the value set as the slow-motion display rate SDR to the shift period calculation section 13.

The shift period calculation section 13 detects that images are acquired at a predetermined frame rate FRA based on an image pickup control signal outputted from the image pickup control section 4. Further, the shift period calculation section 13 calculates a shift period $\beta$ to be used in shifting a light emission interval of the light emitting section 10 by multiplying a reciprocal of the predetermined frame rate FRA detected as described above by a reciprocal of the slow-motion display rate SDR outputted from the user I/F section 12, and outputs a calculated value of the shift period $\beta$ to the light emission signal generating section 8. Specifically, for example, when the predetermined frame rate FRA is 60 fps and the value of the slow-motion display rate SDR is "2", the shift period $\beta$ is calculated as $\frac{1}{120}$ second.

Subsequently, an operation that is performed in the image pickup system 103 will be described with respect to a case of picking up an image of vocal cords as objects, as an example. FIG. 7 is a diagram for explaining an example of the operation performed in the image pickup system according to the third embodiment.

A user arranges the image pickup section 1 and the sound detecting section 6 in the vicinity of the vocal cords which are periodically operating (vibrating), and thereby causes the CMOS sensor 1A to pick up an image of the vocal cords and the sound detecting section 6 to detect a sound generated by the vocal cords.

The synchronous signal generating section 1B generates a synchronous signal in synchronism with timing concerning the image pickup operation of the CMOS sensor 1A, and outputs the signal to (the signal processing section 2 and) the light emission period control section 5. Further, the fundamental period detecting section 7 detects a fundamental period in accordance with a fundamental wave of a sound signal outputted from the sound detecting section 6, and generates a fundamental period signal in accordance with the detected fundamental period and outputs the fundamental period signal to the light emission signal generating section 8.

Incidentally, as schematically shown in FIG. 7, in the image pickup operation by the rolling shutter system, the first pixel located at one end of the line L1 is exposed at timing of time T31, the second to (P-1)th pixels which are located at intermediate positions of the line L1 are sequentially exposed in a period after the time T31, and the Pth pixel located at the other end of the line L1 is exposed to timing of time T33. Then, at timing of the time T33, readout of electric charges accumulated in respective pixels that belong to the line L1 are performed, and exposure on the line L1 is restarted (from the first pixel).

Further, as schematically shown in FIG. 7, in the image pickup operation by the rolling shutter system, the first pixel located at one end of the line LN is exposed at timing of time T32 which is later than the time T31 by a predetermined time period, the second to (P-1)th pixels which are located at intermediate positions of the line LN are sequentially exposed in a period after the time T32, and the Pth pixel located at the other end of the line LN is exposed to timing of time T34 which is later than the time T33 by the predetermined time period. Then, at timing of time T34, readout of electric charges accumulated in respective pixels that belong to the line LN are performed, and exposure on the line LN is restarted (from the first pixel).

That is, according to the image pickup operation in the rolling shutter system as described above, a period from the time T32 to the time T33 can be treated as a period in which exposure for obtaining an image of the same frame is performed on the lines L1-LN of the CMOS sensor 1A. On the other hand, according to the image pickup operation by the rolling shutter system as described above, a period after the time T31 and before the time T32 and a period after the time T33 and before the time T34 can be treated as a period in which exposure for obtaining images of different frames is performed on the lines L1-LN of the CMOS sensor 1A.

The light emission period control section 5 detects exposure states of the respective lines L1-LN from the time T31 to the time T34 (as an exposure state of the CMOS sensor 1A) based on the synchronous signal outputted from the synchronous signal generating section 1B with the image pickup of the vocal cords by the image pickup section 1. Further, the light emission period control section 5 sets the period from the time T32 to the time T33 as a light emission permission period, and sets the period after the time T31 and before the time T32 and the period after the time T33 and before the time T34 as a light emission non-permission period. Then, the light emission period control section 5 generates the light emission period control signal such that a signal level for the light emission permission period and a signal level for the light emission non-permission period are made different as shown in FIG. 7 as an example, and outputs the signal to the light emission control section 9.

The light emission signal generating section 8 specifies a fundamental period BC4 of the sound signal outputted from the sound detecting section 6 based on the fundamental period signal outputted from the fundamental period detecting section 7. Thereafter, the light emission signal generating section 8 determines whether one timing corresponding to time immediately after the fundamental period BC4 and the shift period β elapse belongs to the light emission permission period or the light emission non-permission period, based on the fundamental period BC4 specified as described above, the shift period β outputted from the shift period calculation section 13 and the light emission period control signal outputted from the light emission period control section 5. Then, if a determination result that the one timing corresponding to time immediately after the fundamental period BC4 and the shift period β elapse belongs to the light emission permission period is obtained, the light emission signal generating section 8 generates the stroboscopic light emission signal at the one timing, and outputs the signal to the light emission control section 9. Further, if a determination result that the one timing corresponding to time immediately after the fundamental period BC4 and the shift period β elapse belongs to the light emission non-permission period is obtained, the light emission signal generating section 8 generates the stroboscopic light emission signal at other timing which corresponds to time immediately after the fundamental period BC4 elapses, rather than the one timing, and outputs the signal to the light emission control section 9.

The light emission control section 9 causes the light emitting section 10 to perform a light emission when the stroboscopic light emission signal is inputted in the period from the time T32 to the time T33. Further, the light emission control section 9 nulls (input of) the stroboscopic light emission signal when the stroboscopic light emission signal is inputted in the period after the time T31 and before the time T32 and the period after the time T33 and before the time T34, to cause the light emitting section 10 not to perform a light emission. Thus, with the above control performed in the light emission control section 9, the light emitting section 10 performs light emissions in a light emission state shown in FIG. 7, as an example.

As described above, according to the image pickup system 103 of the present embodiment, the control is performed to cause the light emitting section 10 to perform the stroboscopic light emission during the period in which the exposure for obtaining an image of the same frame is performed on the lines L1-LN of the CMOS sensor 1A, and whereas the control is performed to cause the light emitting section 10 not to perform the stroboscopic light emission during the period in which the exposure for obtaining images of different frames is performed on the lines L1-LN of the CMOS sensor 1A. Therefore, according to the image pickup system 103 of the present embodiment, for example, in a case of observing an object which moves periodically (vibrates periodically) such as vocal cords in a pseudo slow-motion state by performing stroboscopic photographing of the object, it is possible to cause the display section 3 to display an image in which unevenness of brightness within one frame is suppressed.

On the other hand, according to the image pickup system 103 of the present embodiment, the control is performed such that the light emitting section 10 is caused to perform the light emission only when one timing corresponding to time immediately after the fundamental period BC4 and the shift period β elapse is in the light emission permission period. Therefore, according to the image pickup system 103 of the present embodiment, for example, in a case of observing an object which moves periodically (vibrates periodically) such as vocal cords in a pseudo slow-motion state by performing stroboscopic photographing of the object, it is possible to cause the display section 3 to display an image in which continuousness between the respective frames is secured.

That is, according to the image pickup system 103 of the present embodiment, when performing stroboscopic photographing of an object which operates periodically, deterioration of image quality which is caused by the image pickup operation by the rolling shutter system can be suppressed.

It is noted that the present invention is not limited to the foregoing embodiments and it is a matter of course that various modifications and applications are possible within a rage not departing from the gist of the present invention.

What is claimed is:

1. An image pickup system comprising:
  a light source configured to emit light for illuminating an object which operates periodically;
  an image sensor configured to perform an image pickup operation by a rolling shutter system;
  at least one controller comprising hardware, the at least one controller being configured to:
    detect a period of motion of the object;
    generate a stroboscopic light emission signal for causing the light source to perform stroboscopic light emission in synchronism with the detected period of the motion;

set a first period in which exposure for obtaining a first image of the same frame is performed on respective lines of the image sensor, as a light emission permission period;

set a second period in which exposure for obtaining second images of different frames is performed on the respective lines of the image sensor, as a light emission non-permission period;

control the light source to emit light in accordance with the stroboscopic light emission signal when the stroboscopic light emission signal is inputted in the light emission permission period;

control the light source not to emit the light when the stroboscopic light emission signal is inputted in the light emission non-permission period;

compare the light emission permission period and the period of the motion;

responsive to determining that the light emission permission period is longer than the period of the motion, generate a light emission limiting signal for limiting the number of light emissions by the light source in the light emission permission period, or for reducing a light emission amount per one light emission by the light source in accordance with a length of the period of the motion;

responsive to determining that the light emission permission period is equal to or shorter than the period of the motion, generate a frame rate limiting signal for reducing a frame rate concerning acquisition of the first image or the second images to a half of a predetermined frame rate; and control the image sensor to acquire the first image or the second images at the half of the predetermined rate based on the frame rate limiting signal.

2. The image pickup system according to claim 1, wherein the image sensor is further configured to generate a synchronous signal concerning the image pickup operation by the rolling shutter system, and wherein the at least one controller is further configured to detect the first period and the second period based on the generated synchronous signal.

3. The image pickup system according to claim 1, wherein responsive to determining that the light emission permission period is longer than the period of the motion, the at least one controller is further configured to generate the light emission limiting signal for limiting the number of light emissions by the light source in the light emission permission period to one.

4. The image pickup system according to claim 1, wherein the at least one controller is further configured to:

calculate a shift period to be used in shifting a light emission interval of the light source from the period of the motion, based on the predetermined frame rate;

when one timing which corresponds to time immediately after the period of the motion and the shift period elapse belongs to the light emission permission period, generate the stroboscopic light emission signal at the one timing; and when the one timing belongs to the light emission non-permission period, generate the stroboscopic light emission signal at other timing corresponding to time immediately after the period of the motion elapses.

5. The image pickup system according to claim 1, further comprising:

a sound sensor configured to: detect a sound generated by vocal cords as the object; generate a sound signal in accordance with the detected sound; and output the sound signal, wherein the at least one controller is further configured to detect a fundamental period in accordance with a fundamental wave of the sound signal outputted from the sound sensor, as the period of the motion.

6. An image pickup method comprising:

emitting, by a light source, light for illuminating an object which operates periodically;

acquiring, by an image sensor, one or more images using a rolling shutter system;

detecting, by at least one controller comprising hardware, a period of motion of the object;

generating, by the at least one controller, a stroboscopic light emission signal for causing the light source to perform stroboscopic light emission in synchronism with the detected period of the motion;

setting, by the at least one controller, a first period in which exposure for obtaining a first image of the same frame is performed on respective lines of the image sensor, as a light emission permission period;

setting, by the at least one controller, a second period in which exposure for obtaining second images of different frames is performed on the respective lines of the image sensor, as a light emission non-permission period;

controlling, by the at least one controller, the light source to emit light in accordance with the stroboscopic light emission signal when the stroboscopic light emission signal is inputted in the light emission permission period;

controlling, by the at least one controller, the light source not to emit the light when the stroboscopic light emission signal is inputted in the light emission non-permission period;

comparing, by the at least one controller, the light emission permission period and the period of the motion;

responsive to determining that the light emission permission period is longer than the period of the motion, generating, by the at least one controller, a light emission limiting signal for limiting the number of light emissions by the light source in the light emission permission period, or for reducing a light emission amount per one light emission by the light source in accordance with a length of the period of the motion;

responsive to determining that the light emission permission period is equal to or shorter than the period of the motion, generating, by the at least one controller, a frame rate limiting signal for reducing a frame rate concerning acquisition of the first image or the second images to a half of a predetermined frame rate; and controlling, by the at least one controller, the image sensor to acquire the first image or the second images at the half of the predetermined rate based on the frame rate limiting signal.

* * * * *